(12) United States Patent
Ott

(10) Patent No.: US 6,723,104 B2
(45) Date of Patent: Apr. 20, 2004

(54) IOL INSERTION APPARATUS AND METHOD FOR USING SAME

(75) Inventor: Robert D. Ott, Irvine, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 0 days.

(21) Appl. No.: 10/099,843

(22) Filed: Mar. 13, 2002

(65) Prior Publication Data

US 2003/0176870 A1 Sep. 18, 2003

(51) Int. Cl.[7] .................................................. A61F 9/00
(52) U.S. Cl. ...................................................... 606/107
(58) Field of Search .................... 606/99, 107; 623/6.12

(56) References Cited

U.S. PATENT DOCUMENTS

| | | | |
|---|---|---|---|
| 5,616,148 A | * 4/1997 | Eagles et al. | ................ 606/107 |
| 5,643,276 A | 7/1997 | Zaleski | |
| 5,735,858 A | 4/1998 | Makker et al. | |
| 5,800,442 A | 9/1998 | Wolf et al. | |
| 6,010,510 A | 1/2000 | Brown et al. | |
| 6,022,358 A | * 2/2000 | Wolf et al. | .................. 606/107 |
| 6,074,397 A | * 6/2000 | Chambers et al. | ........... 606/107 |
| 6,162,229 A | * 12/2000 | Feingold et al. | ............. 606/107 |
| 6,214,015 B1 | * 4/2001 | Reich et al. | ................. 606/107 |

FOREIGN PATENT DOCUMENTS

JP          5-103809          4/1993

* cited by examiner

*Primary Examiner*—Eduardo C. Robert
(74) *Attorney, Agent, or Firm*—Frank Uxa; Peter J. Gluck

(57) ABSTRACT

Apparatus for inserting intraocular lenses (IOLs) into eyes are disclosed. The apparatus comprises an insertion tube, and an injector rod having a distal tip capable of engaging an intraocular lens. A guide assembly is provided to direct the distal tip of the rod radially outwardly as it moves distally through the insertion tube. The radial movement of the tip is controlled such that the tip contacts a proximal edge, rather than a fold, of the IOL. The tip exerts little or no pressure on the bottom wall of the IOL cartridge, with any incidental pressure varying as the tip moves distally. In one embodiment, the guide assembly also includes a component for allowing the tip to return upward after contacting the IOL, thus decreasing or eliminating the pressure on the wall as the rod tip continues through a narrower diameter exit portion of the cartridge. Methods for inserting an IOL into an eye using such apparatus are also disclosed and are within the scope of the present invention.

3 Claims, 2 Drawing Sheets

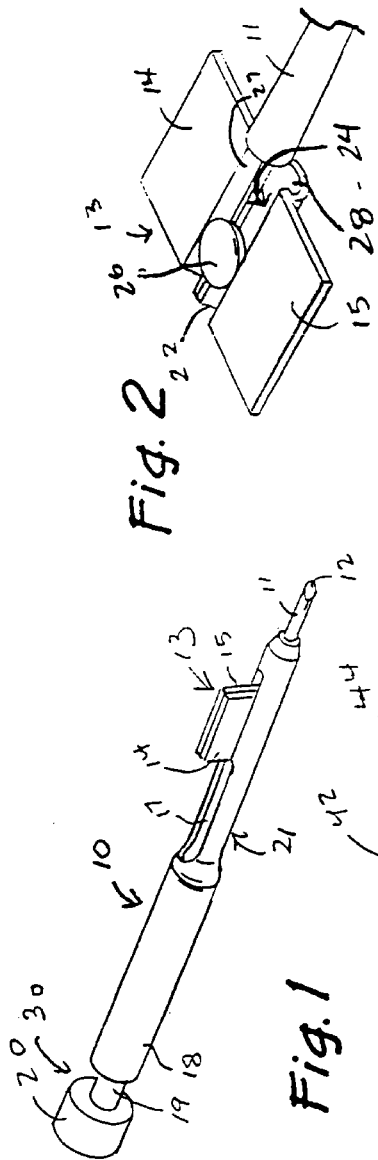
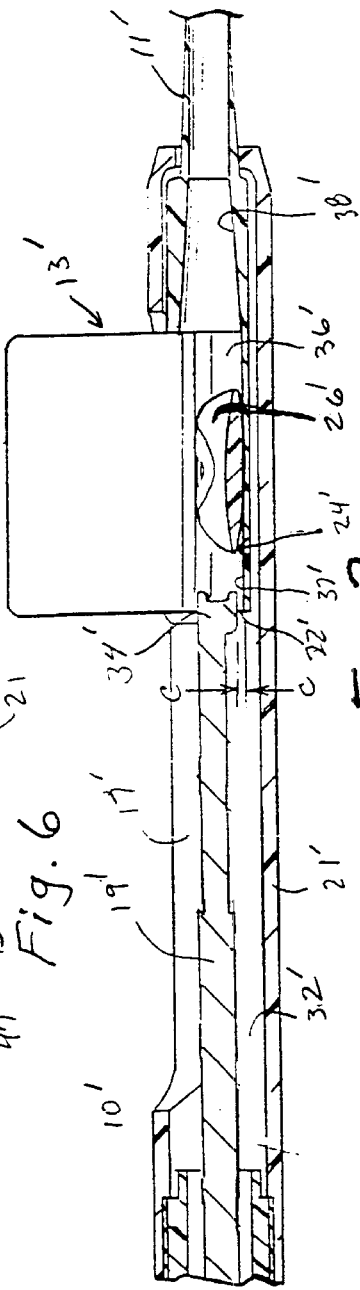

IOL INSERTION APPARATUS AND METHOD FOR USING SAME

BACKGROUND OF THE INVENTION

The present invention relates to apparatus and methods for inserting an intraocular lens through a small incision into an eye. More particularly, the invention relates to such apparatus and methods wherein insertion of the lens is accomplished with minimum potential for damage to the lens.

An intraocular lens (IOL) is implanted in the eye, for example, as a replacement for the natural crystalline lens after cataract surgery or to alter the optical properties of (provide vision correction to) an eye in which the natural lens remains. IOLs often include an optic, and preferably at least one flexible fixation member or haptic, which extends from the optic and becomes affixed in the eye to secure the lens in position. The optic normally includes an optically clear lens. Implantation of such IOLs into the eye often involves making an incision in the eye. Making the incision as small as possible reduces trauma and speeds healing.

IOLs are known which are foldable (deformable) so that the IOL can be inserted into the eye through an incision smaller than the diameter of the lens.

Some of the most generally accepted insertion apparatus employ a hollow insertion tube having a diameter which permits the folded IOL to pass freely through the tube without permanent deformation. In these generally accepted apparatus, the insertion tube is held in a handpiece which is coupled to a plunger rod. The plunger rod is moved distally through the insertion tube to urge the IOL to pass through the tube and into the eye.

Several disadvantages are apparent in such insertion devices. For example, pushing, without trapping or holding, the IOL through and out of the hollow space defined by the tube can cause the IOL to be released from the insertion device without precise control, so that the released IOL may damage the eye and/or may be mispositioned in the eye. In addition, the rod may scratch and/or even tear the optic. Alternatively, the trailing haptic may become wedged between the rod and the plunger tip, resulting in permanent deformation of the haptic.

Various plunger tip configurations have been devised to minimize the potential for scratching and/or tearing the optic of an IOL. In U.S. Pat. No. 5,735,858, for instance, Makker et al. disclose a tip formed of an elastomeric silicone polymer composition which is softer and more elastic than the plunger rod. The tip has a distally tapered configuration which allows the tip to enter a fold of the folded IOL more effectively and efficiently than prior art tips, and to become held or trapped by the folded IOL. This allows the IOL to be carried and/or pulled, rather than pushed, by the rod/tip combination, giving a surgeon more control of the movement of the IOL through the hollow passage of the insertion tube and the release of the IOL into the eye. Also, because the proximal end of the tip can have a relatively large cross-sectional area, the rod itself can have a reduced cross-sectional area, thus minimizing the tendency of the rod to damage the lens.

The soft-tip plunger disclosed by Makker et al. is particularly suitable for use with IOLs having optics made of elastomeric silicone polymeric materials. In recent years, however, lenses having optics made of acrylic-based polymeric materials have increased in popularity, partly due to their tendency to regain their original configuration relatively slowly after being inserted in an eye in a folded condition. This delayed unfolding allows the surgeon more time to properly position the IOL in the eye after insertion so that controlled release of the IOLs from the inserter is somewhat less important.

IOLs having optics made of acrylic-based material are more susceptible to scratching and other types of damage than IOLs having optics made of silicon-based materials. In addition, acrylic materials tend to be more adherent, which increases the likelihood that a folded lens will stick to the a wall of the injector tube bore, allowing the plunger tip to advance without advancing the IOL. As a result, even when very soft tip materials are used, insertion apparatus of the type disclosed by Makker at al., which introduce at least a portion of the tip into a fold of the folded IOL, are less appropriate for use with acrylic lenses than with silicone lenses. Still another disadvantage of acrylic IOLs is their decreased flexibility relative to silicon IOLs. Because acrylic IOLs can not be folded as compactly as silicon IOLs, injectors for acrylic IOLs must be provided with larger diameter bores. The larger bores require larger diameter tips, which in turn require larger incisions in the patient's eye.

U.S. Pat. No. 6,010,510 to Brown et al. discloses an injector designed to optimize performance with soft acrylic IOLs. Specifically, the plunger of the Brown et al. injector has a blunt, rounded tip offset from the centerline of the plunger tod. The offset tip assures that the tip is biased downward against the bottom of the cartridge bore, thus exerting constant pressure against the wall of the bore. This arrangement helps prevent the tip from riding up over the IOL and being folded within the IOL.

A potential disadvantage of the plunger design disclosed by Brown et al. is that the constant pressure exerted on the wall of the bore by the tip of the plunger results in frictional forces which the surgeon must overcome by exerting more opposing force on the plunger than would be required if there were a clearance between the plunger tip and the wall. The possibility of damage to the IOL, the wall of the cartridge, or even the IOL recipient's eye may be increased as a result of this additional force.

It would therefore be advantageous to provide IOL insertion apparatus and methods which facilitate the insertion of the IOL in the eye in an easy, effective and controlled manner while avoiding damage to the IOL and undue trauma to the patient.

SUMMARY OF THE INVENTION

New apparatus for inserting IOLs and methods for inserting IOLs have been discovered. The present apparatus and methods address one or more of the concerns of the prior art systems, such as those noted above. The present apparatus enable the surgeon to advance the plunger of an insertion apparatus through the passage of a closed IOL cartridge with minimal force, thus reducing the risk of damaging the IOL, the IOL cartridge, or the recipient's eye. The present invention is straightforward, easy to produce and practice, and involves little or no modification of surgical techniques. In other words, surgeons need not learn a different surgical procedure for inserting an IOL into the eye, nor does the IOL need to be modified to accommodate the present apparatus and methods.

In one broad aspect, the present invention comprises apparatus for inserting IOLs into an eye which include a tube, such as an insertion tube or cartridge, defining a hollow passage, for example, through at least a portion of which a folded IOL can be moved. This tube has an ejection port or opening, preferably at the distal end of the tube, from which the IOL is passed for insertion into an eye. An injector rod is also included and is longitudinally or axially movable within the hollow passage of the tube. The distal segment of the rod is adapted to urge the folded IOL distally through the passage, for example, by contacting the folded IOL as the distal segment of the rod passes distally in the passage. A guide assembly is provided for directing the distal segment of the rod radially outwardly, toward the bottom of hollow passage, as it progresses along the tube. This deflection of the tip of the rod toward the bottom of the passage ensures that the rod contacts a proximal edge, rather than a fold, of the folded IOL, thus reducing the likelihood that the tip will bypass or damage the IOL, and allowing less volume inside the cartridge. Further, the guide assembly allows a certain amount of "play" so that the rod tip makes minimal, if any, initial contact with the passage wall, and exerts little or no pressure on the wall.

In one embodiment, the guide assembly comprises a projection such as a guide pin, depending from an inner wall of the injector handpiece and cooperating with an outer surface of the injector rod to direct the distal tip of the rod radially outwardly. In a particularly useful embodiment, at least a portion of the proximal end of the rod is tapered to allow the tip to rise gradually after contacting the proximal edge of the IOL. This prevents the tip from scraping the bottom edge wall of the injector cartridge, and is especially desirable in cases where the cartridge has a distally tapered ejection port.

In another broad aspect of the invention, a method of preparing an IOL for insertion into an eye is provided. The method comprises the steps of:

placing an intraocular lens in a folded condition in an insertion apparatus having a tube defining a hollow passage having an ejection opening, and an injector rod longitudinally movable within the hollow portion of the tube, the injector rod having a distal tip;

advancing the injector rod distally and radially outwardly toward a wall of the hollow passage to allow the distal tip of the injector rod to contact a proximal edge of the folded intraocular lens; and continuing to advance the injector rod distally to urge the folded intraocular lens toward the ejection opening of the apparatus.

The step of continuing to advance the injector rod distally may also include a step of allowing the tip of the rod to return upwardly, away from the wall of the hollow passage, after contacting the proximal edge of the IOL.

Insertion apparatus as disclosed elsewhere herein are particularly useful in practicing the present methods.

Each and every feature described herein, and each and every combination of two or more of such features, is included within the scope of the present invention provided that the features included in such a combination are not mutually inconsistent.

These and other aspects of the present invention will become apparent in the following detailed description and claims, particularly when considered in conjunction with the accompanying drawings in which like parts bear like reference numerals.

BRIEF DESCRIPTION OF THE DRAWINGS

FIG. 1 is a side perspective view of an insertion apparatus in accordance with the present invention.

FIG. 2 is a perspective view of an injection cartridge shown in an open position.

FIG. 3 is an enlarged fragmentary side cross-sectional view of the distal portion of a prior art insertion apparatus;

FIG. 6 is an enlarged fragmentary side cross-sectional view showing a guide assembly accordance with an alternate embodiment of the present invention.

DETAILED DESCRIPTION OF THE PREFERRED EMBODIMENTS

Figure 4:
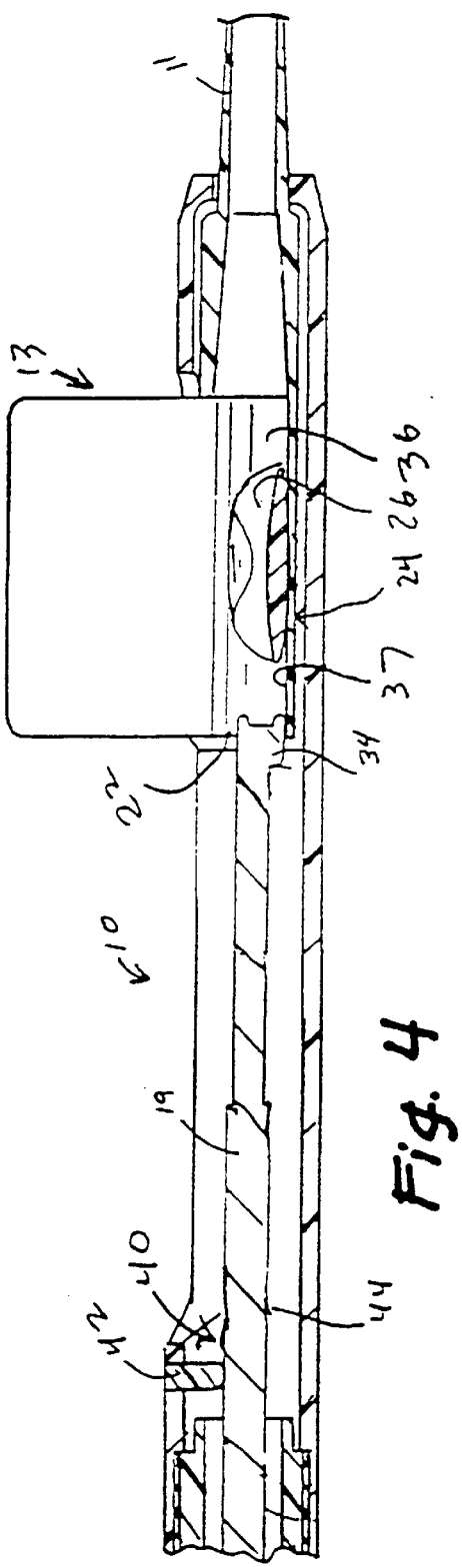
FIG. 4 is an enlarged fragmentary side cross-sectional view of the distal portion of an apparatus in accordance with the present invention, showing the injector rod prior to contact with a folded IOL.

FIG. 1 illustrates an IOL insertion apparatus, shown generally as 10. The apparatus 10 comprises body or handpiece 21, and a folding cartridge 13 including a forward tube 11 having an ejector port 12 at its distal end. The handpiece 21 of injection apparatus 10 is an integrally formed unit. Folding cartridge 13 has folding leaves 14 and 15 which extend through opening 17 in the outer wall of the handpiece 21. Proximal end portion 18 can be sized to completely and closely encompass plunger 19 of injector rod-plunger assembly 30, which has a plunger cap 20 affixed to its proximal end.

FIG. 2 shows lens cartridge 13 in greater detail. The cartridge 13 includes forward tube 11, an entry port 22, and a loading area 24 consisting of folding members 27 and 28. An IOL 26 is placed in an unfolded state on folding members 27 and 28 using suitable means such as forceps (not shown). Hinged folding leaves 14 and 15 are moved together, folding the flexible IOL 26 in half, before the cartridge 13 is inserted into the opening 17 of the injector handpiece 21.

A prior art insertion apparatus 10' is shown in FIG. 3. The apparatus 10' includes plunger 19' mounted for longitudinal movement in bore 32' of handpiece 21'. Plunger 19' has a distal tip 34', the diameter of which typically measures around 0.085". The diameter of the loading portion of passage 36' through the folded lens cartridge 13' is approximately 0.1", leaving a clearance c—c of about 0.015" between the bottom surface of the plunger tip 34' and the bottom wall 37' of passage 36' at entry port 22'. Clearance c—c remains substantially constant as the plunger tip 34' advances through loading area 24' and gradually decreases as the plunger continues through a tapered transition portion 38' leading to the forward tube 11' of the cartridge 13'.

In an embodiment of the present invention shown in FIG. 4, IOL insertion apparatus 10 is provided with a guide assembly 40' which directs the distal tip 34 of the plunger 19 radially outwardly to reduce or eliminate clearance c—c. As illustrated, the guide assembly 40' comprises a projecting member 42 which cooperates with the outer surface 44 of the plunger 19 to direct the tip 34 toward the bottom wall 37 of passage 36. Preferably, the length and location of projecting member 42 are selected to allow "play" between the distal tip 34 of plunger 19 and the wall 37. If the rod tip 34 does contact the wall 37, such contact should occur just as, or slightly after, the tip 34 crosses entry port 22, and should be light, so that the tip 34 initially exerts little or no pressure on the wall 37. Guide pin 42 acts essentially as a fulcrum, with the portion of the rod 19 between the guide pin 42 and the distal tip 34 defining a lever arm. The length of the lever arm increases as the tip 34 travels through the loading area 24 of the cartridge 13, thus allowing for variations in the amount of pressure exerted on the wall 37.

In the illustrated embodiment, the projecting member 42 is a guide pin which may be easily retrofit into the handpiece 21 of an existing insertion apparatus 10. However, projecting member 42 may also be formed as a protrusion integral with or otherwise secured to an inner wall of the handpiece 21. It is also possible to position the projection member 42 so some clearance c—c between the distal tip 34 of the rod 19 and the wall 37 of the passage 36 remains. In this case, the projection member 42 would not cause the distal tip 34 of the rod 19 to contact the wall 37, but would merely prevent the distal tip 34 from rising above a certain level and riding over the IOL.

Figure 5:
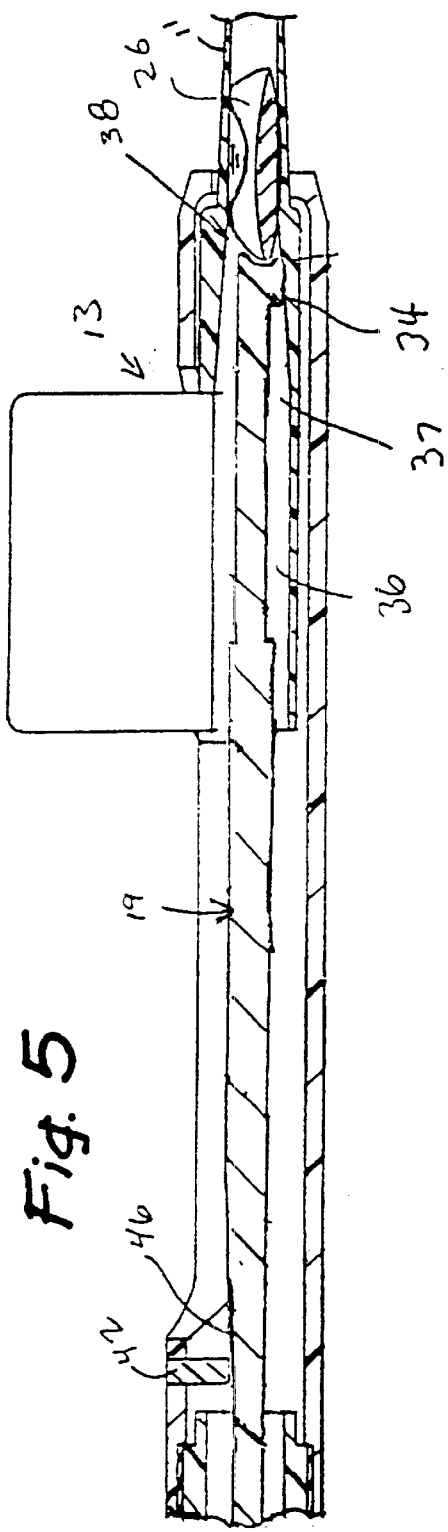
FIG. 5 is an enlarged fragmentary side cross-sectional view of the distal portion of the apparatus in accordance with a preferred embodiment of the present invention, showing the injector rod after contacting the folded IOL.

FIG. 5 shows an embodiment of the invention wherein the plunger rod 19 is modified to have a tapered proximal surface 46. Projecting member 42 cooperates with tapered proximal surface 46 to allow the distal tip 34 to return upward after contacting the proximal edge of IOL 26. This reduces the amount of force needed to eject the IOL 26 through the ejection port, and minimizes the possibility of the tip 34 scraping or otherwise damaging the wall 37 of the passage 36 as the tip 34 advances through the tapered transition portion 38 of the cartridge 13. The tapered walls of the transition portion 38 compress the IOL 26 into a more tightly folded configuration as it advances down the passage 36. This allows use of a forward tube 11 having a smaller cross-sectional area than was previously possible, thus requiring a smaller incision in the eye, faster healing time, and less trauma to the IOL recipient.

In still another embodiment of the invention, shown in FIG. 6, an additional guide pin 43 is inserted through the bottom wall 47 of the handpiece body 21, at a location circumferentially opposite the first guide pin 42. The second guide pin 43 exerts an upward force on the bottom of the injector rod 44, thus opposing the downward force exerted by the first guide pin 42 to maintain the rod 44 in a centered position. This embodiment may be preferred for use with silicone IOLs, where it is desirable to engage a fold, rather than an edge, of the lens. The guide pins 42 and 43 could also be positioned on opposite sides, rather than the top and bottom of the handpiece body 21, in situations where horizontal centering of the rod 44 is more important than vertical centering. Alternatively, 3 or more guide pins could be provided at regular, circumferentially spaced-apart intervals around the handpiece body 21 in situations where both horizontal and vertical centering is desired.

The configuration of the tip 34 shown in FIGS. 4 and 5 is merely exemplary, as the guide assembly 40 disclosed in connection with the insertion apparatus 10 of the present invention is not limited to use with plungers having any particular type of tip. It can be retrofit into injectors having either soft or metal tip plungers. It is particularly useful, however, for use with metal tip plungers of the type commonly used for acrylic IOLs, since the soft, adherent nature of acrylic material makes it more critical that the plunger tip contact an edge, rather than a fold, of the IOL.

The present IOL insertion apparatus and methods effectively and straightforwardly control the advance of an injector rod through a tube of the apparatus. This control is achieved without undue reliance on the technique and/or dexterity of the surgeon and without undue risk of damaging the IOL being inserted. Controlling the advance of the injector rod through the tube reduces the risk of damage to the IOL, the IOL cartridge, or the IOL recipient's eye. Furthermore, the apparatus and methods disclosed herein do not require significant redesign of existing plungers. The simplest embodiment of the apparatus can in fact be manufactured relatively inexpensively by making a single modification to a prior art handpiece.

While this invention has been described with respect to various specific examples and embodiments, it is to be understood that the invention in not limited thereto and that it can variously be practiced within the scope of the following claims.

What is claimed is:

1. An apparatus for inserting an intraocular lens through an incision into any eye comprising:

a tube defining a hollow passage, the tube having an ejection port through which the intraocular lens is passed from the hollow passage into an eye;

an injector rod longitudinally movable within the hollow passage, the injector rod having a distal portion adapted to contact the intraocular lens within the hollow passage to urge the folded intraocular lens distally through the hollow passage;

a guide assembly positioned relative to the tube to maintain the injector rod in a desired orientation with respect to the passage as the injector rod is moved longitudinally in the passage; and, wherein the guide assembly comprises a projection depending from an inner surface of the tube, the projection cooperating with a surface of the rod to move the distal portion of the rod toward the wall as the injector rod is moved longitudinally in the passage.

2. An apparatus for inserting an intraocular lens through an incision into any eye comprising:

a tube defining a hollow passage, the tube having an ejection port through which the intraocular lens is passed from the hollow passage into an eye;

an injector rod longitudinally movable within the hollow passage, the injector rod having a distal portion adapted to contact the intraocular lens within the hollow passage to urge the folded intraocular lens distally through the hollow passage:

a guide assembly positioned relative to the tube to maintain the injector rod in a desired orientation with respect to the passage as the injector rod is moved longitudinally in the passage; and, wherein the guide assembly comprises a projection depending from an inner surface of the tube, the projection cooperating with a distal surface of the rod to direct the distal portion of the rod toward the wall as the injector rod is moved longitudinally in the passage; and the component comprises a tapered proximal surface of the rod, the projection cooperating with the tapered proximal surface to allow the distal tip to gradually rise after contacting the intraocular lens.

3. An intraocular lens system, comprising:

a handpiece having an injector rod, the injector rod having a distal tip;

an injection cartridge defining a passage, the cartridge to be received in the handpiece so that the injector rod can travel down the passage, the passage including an entry port for facing a proximal end of the handpiece;

a loading area for holding a folded intraocular lens;

an ejection port through which the intraocular lens is injected into an eye;

a guide assembly positioned relative to the tube to maintain the injector rod in a desired orientation with respect to the passage as the injector rod is moved longitudinally in the passage; and wherein the guide assembly directs the distal tip of the injector rod radially outwardly toward a wall of the passage as the injector rod is moved longitudinally in the passage; and wherein the guide assembly is coupled to the handpiece and cooperates with a surface of the rod to direct the distal tip of the rod toward the wall; and wherein the guide assembly comprises a projection depending from an inner surface of the handpiece proximally of the cartridge, the projection cooperating with a surface of the rod to move the distal tip of the rod toward the wall.

* * * * *